(12) United States Patent
Maclaren et al.

(10) Patent No.: US 9,834,788 B2
(45) Date of Patent: Dec. 5, 2017

(54) AAV -VECTORS FOR USE IN GENE THERAPY OF CHOROIDEREMIA

(75) Inventors: Robert Maclaren, Oxford (GB); Miguel Seabra, London (GB); Matthew John During, Columbus, OH (US)

(73) Assignee: Oxford University Innovation Limited, Oxford (GB)

( * ) Notice: Subject to any disclaimer, the term of this patent is extended or adjusted under 35 U.S.C. 154(b) by 205 days.

(21) Appl. No.: 14/000,836

(22) PCT Filed: Feb. 21, 2012

(86) PCT No.: PCT/GB2012/050376
§ 371 (c)(1),
(2), (4) Date: Dec. 18, 2013

(87) PCT Pub. No.: WO2012/114090
PCT Pub. Date: Aug. 30, 2012

(65) Prior Publication Data
US 2014/0107185 A1    Apr. 17, 2014

(30) Foreign Application Priority Data
Feb. 22, 2011    (GB) .................................. 1103062.4

(51) Int. Cl.
*C12N 15/86* (2006.01)
*C12N 9/10* (2006.01)
*A61K 48/00* (2006.01)

(52) U.S. Cl.
CPC ............ *C12N 15/86* (2013.01); *A61K 48/005* (2013.01); *C12N 9/1085* (2013.01); *C12N 2750/14143* (2013.01); *C12N 2750/14171* (2013.01)

(58) Field of Classification Search
CPC .................. C12N 15/861; C12N 15/86; C12N 2750/14143; C12N 2750/14171; C12N 9/1085; A61K 48/005
See application file for complete search history.

(56) References Cited

U.S. PATENT DOCUMENTS

| | | | |
|---|---|---|---|
| 6,232,105 B1 | 5/2001 | Einerhand et al. | |
| 8,278,284 B2 * | 10/2012 | Miyazaki ............ | A61K 48/005 424/93.1 |
| 2004/0208847 A1 * | 10/2004 | Rolling ............... | A61K 48/0075 424/93.2 |
| 2009/0074723 A1 * | 3/2009 | Acland ................. | C12N 15/86 424/93.2 |
| 2009/0202505 A1 * | 8/2009 | Bartus ................ | A61K 31/7088 424/93.21 |

FOREIGN PATENT DOCUMENTS

| | | |
|---|---|---|
| WO | WO2001068888 A2 * | 11/2001 |
| WO | 2004/084951 | 10/2004 |
| WO | 2009/097129 | 8/2009 |
| WO | 2011/088081 | 7/2011 |

OTHER PUBLICATIONS

Anand et al. "Gene therapy for choroideremia: in vitro rescue mediated by recombinant adenovirus."Vision Res. Apr. 2003;43(8):919-26.*
Rolling, F. "Recombinant AAV-mediated gene transfer to the retina: gene therapy perspectives." Gene Ther. Oct. 2004;11 Suppl 1:S26-32.*
Surace and Auricchio et al. "Versatility of AAV vectors for retinal gene transfer." Vision Res. Feb. 2008;48(3):353-9. Epub Oct. 17, 2007.*
Gaudana et al. "Ocular drug delivery." AAPS J. Sep. 2010;12(3):348-60.*
Reich and Bennett. "Gene therapy for ocular neovascularization: a cure in sight."Curr Opin Genet Dev. Jun. 2003;13(3):317-22.*
Martin et al. "Gene delivery to the eye using adeno-associated viral vectors."Methods. Oct. 2002;28(2):267-75.*
Rudinger "Characteristics of the amino acids as components of a peptide hormone sequence.", JA Parsons, Ed., 1976, pp. 1-7.*
Imai et al. "Protein Seq Data Anal. Feb. 1989;2(2):81-6." Protein Seq Data Anal. Feb. 1989;2(2):81-6.*
van Bokhoven et al. "Cloning and characterization of the human choroideremia gene."Hum. Mol. Genet. (1994) 3 (7): .Abstract.*
Tolmachova et al. "Gene Therapy Studies in the Mouse Model of Choroideremia." Human Gene Therapy. Apr. 2009, 20(4): 396-422. P33, p. 407.*
Bennicelli et al. "Reversal of blindness in animal models of leber congenital amaurosis using optimized AAV2-mediated gene transfer." Mol Ther. Mar. 2008;16(3):458-65.*
T. Tolmachova et al: "Retinal Pigment Epithelium Detects Accelerate Photoreceptor Degeneration in Cell Type-Specific Knockout Muse Models of Choroideremia", Investigative Ophthalmology & Visiual Science, vol. 51, No. 10, Oct. 1, 2010, pp. 4913-4920.
Albert M. Maguire et al: Safety and Efficacy of Gene Transfer for Leber's Congenital Amaurosis, New England Journal of Medicine, vol. 358, No. 21, May 22, 2008, pp. 2240-2248.
William W. Hauswirth et al: Treatment of Leber Congenital Amaurosis Due to RPE65 Mutations by Ocular Subretinal Injection of Adeno-Associated Virus Gene Vector: Short-Term Results of A Phase I Trial; Human Gene Therapy 19-979-990 (Oct. 2008).
Allocaa, et al., "Novel Adeno-Associated Virus Serotypes Efficiently Transduce Murine Photoreceptors", Journal of Virology, vol. 81, No. 20, 2007, 11372-11380.
Altschul, "A Protein Alignment Scoring System Sensitive at All Evolutionary Distances", J. Mol. Evol., vol. 36, 1993, 290-300.
Altschul, et al., "Basic Local Alignment Search Tool", J. Mol. Biol., vol. 215, 1990, 403-410.
Bainbridge, et al., "Effect of Gene Therapy on Visual Function in Leber's Congenital Amaurosis", The New England Journal of Medicine, vol. 358, 2008, 2231-2239.
Choi, et al., "AAV Hybrid Serotypes: Improved Vectors for Gene Delivery", Curr Gene Ther, vol. 5, No. 3, 2005, 299-310.
Coura, et al., "The State of the Art of Adeno-Associated Virus-Based Vectors in Gene Therapy", Virology Journal, vol. 4, No. 99, 2007, 1-7.

(Continued)

*Primary Examiner* — Titilayo Moloye
(74) *Attorney, Agent, or Firm* — Cooley LLP; Ivor R. Elrifi; Katherine J. Miller

(57) ABSTRACT

The present invention relates to gene therapy for treatment or prevention of choroideremia.

10 Claims, 2 Drawing Sheets

(56) References Cited

OTHER PUBLICATIONS

Cronin, et al., "Functional Genomics Study of the RdCVF-/- Mouse Model", Investigative Ophthalmology & Visual Science, vol. 49, No. 3058, 2008, D1048.
Devereux, "A Comprehensive Set of Sequence Analysis Programs for the VAX", Nucleic Acids Research, vol. 12, No. 1, 1984, 387-395.
Laughlin, et al., "Spliced Adenovirus-Associated Virus RNA", Proc. Natl. Acad. Sci. USA, vol. 76, No. 11, 1979, 5567-5571.
MacLaren, et al., "Retinal Gene Therapy in Patients with Choroideremia: Initial Findings From a Phase 1/2 Clinical Trial", The Lancet, vol. 383, No. 9923, 2014, 1129-1137.
Mancuso, et al., "Gene Therapy for Red-Green Colour Blindness in Adult", Nature, vol. 461, No. 7265, 2009, 784-787.
Wu, et al., "Adeno-associated Virus Serotypes: Vector Toolkit for Human Gene Therapy", Molecular Therapy vol. 14, No. 3, 2006, 316-327.
Tanya Tolmachova, et al., "Independent degenerative of photoreceptors and retinal pigment epithelium in conditional knock-out mouse models of choroideremia", The Journal of Clinical Investigation, vol. 116, No. 2, pp. 386-394 (Feb. 2006).
Bennett, et al. "Stable transgene expression in rod photoreceptors after recombinant adeno-associated virus-mediated gene transfer to monkey retina", Proc Natl Acad Sci USA, Aug. 17, 1999; 96(17) 9920-9925.
Syed et al., Evaluation of Retinal Photoreceptors and Pigment Epithelium in a Female Carrier of Choroideremia, Ophthalmology, Apr. 2001, pp. 711-720, vol. 108, No. 4.
Rak et al., Structure of the Rab7:REP-1 Complex: Insights into the Mechanism of Rab Prenylation and Choroideremia Disease, Cell, Jun. 11, 2004, pp. 749-60, vol. 117.
Boye et al., A Comprehensive Review of Retinal Gene Therapy, Molecular Therapy, Mar. 2013, pp. 509-519, vol. 21, No. 3.
Edwards et al., Visual Acuity after Retinal Gene Therapy for Choroideremia, The New England Journal of Medicine, May 19, 2016, vol. 374, No. 20 with Supplementary Appendix.

* cited by examiner

SEQUENCE LISTING

<160> NUMBER OF SEQ ID NOS: 9

<210> SEQ ID NO 1
<211> LENGTH: 4679
<212> TYPE: DNA
<213> ORGANISM: adeno-associated virus 2

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
```

```
gccaactcca tcactagggg ttcctggagg ggtggagtcg tgacgtgaat tacgtcatag      180
ggttagggag gtcctgtatt agaggtcacg tgagtgtttt gcgacatttt gcgacaccat      240
gtggtcacgc tgggtattta agcccgagtg agcacgcagg gtctccattt tgaagcggga      300
ggtttgaacg cgcagccgcc atgccggggt tttacgagat tgtgattaag gtccccagcg      360
accttgacga gcatctgccc ggcatttctg acagctttgt gaactgggtg gccgagaagg      420
aatgggagtt gccgccagat tctgacatgg atctgaatct gattgagcag gcaccccctga     480 ccgtggccga gaagctgcag cgcgactttc tgacggaatg gcgccgtgtg agtaaggccc      540 cggaggcccct tttctttgtg caatttgaga agggagagag ctacttccac atgcacgtgc     600
tcgtggaaac caccggggtg aaatccatgg ttttgggacg tttcctgagt cagattcgcg      660
aaaaactgat tcagagaatt taccgcggga tcgagccgac tttgccaaac tggttcgcgg      720
tcacaaagac cagaaatggc gccggaggcg ggaacaaggt ggtggatgag tgctacatcc      780
ccaattactt gctccccaaa acccagcctg agctccagtg ggcgtggact aatatggaac      840
agtatttaag cgcctgtttg aatctcacgg agcgtaaacg gttggtggcg cagcatctga      900
cgcacgtgtc gcagacgcag gagcagaaca aagagaatca gaatcccaat tctgatgcgc      960
cggtgatcag atcaaaaact tcagccaggt acatggagct ggtcgggtgg ctcgtggaca      1020 agggggattac ctcggagaag cagtggatcc aggaggacca ggcctcatac atctccttca    1080
atgcggcctc caactcgcgg tcccaaatca aggctgcctt ggacaatgcg ggaaagatta     1140
tgagcctgac taaaaccgcc cccgactacc tggtgggcca gcagcccgtg gaggacattt     1200
ccagcaatcg gatttataaa attttggaac taaacgggta cgatccccaa tatgcggctt     1260
ccgtctttct gggatgggcc acgaaaaagt tcggcaagag gaacaccatc tggctgtttg     1320
ggcctgcaac taccgggaag accaacatcg cggaggccat agcccacact gtgcccttct     1380
acgggtgcgt aaactggacc aatgagaact ttcccttcaa cgactgtgtc gacaagatgg     1440
tgatctggtg ggaggagggg aagatgaccg ccaaggtcgt ggagtcggcc aaagccattc     1500
tcggaggaag caaggtgcgc gtggaccaga atgcaagtc ctcggcccag atagacccga     1560
ctcccgtgat cgtcacctcc aacaccaaca tgtgcgccgt gattgacggg aactcaacga     1620
ccttcgaaca ccagcagccg ttgcaagacc ggatgttcaa atttgaactc acccgccgtc     1680
tggatcatga ctttgggaag gtcaccaagc aggaagtcaa agactttttc cggtgggcaa     1740
aggatcacgt ggttgaggtg gagcatgaat tctacgtcaa aaagggtgga gccaagaaaa     1800
gacccgcccc cagtgacgca gatataagtg agcccaaacg ggtgcgcgag tcagttgcgc     1860
agccatcgac gtcagacgcg gaagcttcga tcaactacgc agacaggtac caaaacaaat     1920
gttctcgtca cgtgggcatg aatctgatgc tgtttccctg cagacaatgc gagagaatga     1980
atcagaattc aaatatctgc ttcactcacg gacagaaaga ctgtttagag tgctttcccg     2040
tgtcagaatc tcaacccgtt tctgtcgtca aaaaggcgta tcagaaactg tgctacattc     2100
atcatatcat gggaaaggtg ccagacgctt gcactgcctg cgatctggtc aatgtggatt     2160
tggatgactg catctttgaa caataaatga tttaaatcag gtatggctgc cgatggttat     2220
cttccagatt ggctcgagga cactctctct gaaggaataa gacagtggtg gaagctcaaa    2280
cctggcccac caccaccaaa gcccgcagag cggcataagg acgacagcag ggtcttgtg     2340 cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt ttcaggagcg ccttaaagaa    2520
```

```
gatacgtctt ttgggggcaa cctcggacga gcagtcttcc aggcgaaaaa gagggttctt      2580
gaacctctgg gcctggttga ggaacctgtt aagacggctc cgggaaaaaa gaggccggta      2640
gagcactctc ctgtggagcc agactcctcc tcgggaaccg gaaaggcggg ccagcagcct      2700
gcaagaaaaa gattgaattt tggtcagact ggagacgcag actcagtacc tgaccccag       2760 cctctcggac agccaccagc agcccctct ggtctgggaa ctaatacgat ggctacaggc       2820
agtggcgcac caatggcaga caataacgag gcgccgacg gagtgggtaa ttcctcggga       2880
aattggcatt gcgattccac atggatgggc gacagagtca tcaccaccag cacccgaacc      2940
tgggccctgc ccacctacaa caaccacctc tacaaacaaa tttccagcca atcaggagcc      3000
tcgaacgaca atcactactt tggctacagc accccttggg ggtattttga cttcaacaga      3060
ttccactgcc acttttcacc acgtgactgg caaagactca tcaacaacaa ctggggattc      3120
cgacccaaga gactcaactt caagctcttt aacattcaag tcaaagaggt cacgcagaat      3180
gacggtacga cgacgattgc caataacctt accagcacgg ttcaggtgtt tactgactcg      3240
gagtaccagc tcccgtacgt cctcggctcg gcgcatcaag gatgcctccc gccgttccca      3300
gcagacgtct tcatggtgcc acagtatgga tacctcaccc tgaacaacgg gagtcaggca      3360
gtaggacgct cttcatttta ctgcctggag tactttcctt ctcagatgct gcgtaccgga      3420
aacaacttta ccttcagcta cactttgag gacgttcctt ccacagcag ctacgctcac       3480 agccagagtc tggaccgtct catgaatcct ctcatcgacc agtacctgta ttacttgagc      3540
agaacaaaca ctccaagtgg aaccaccacg cagtcaaggc ttcagttttc tcaggccgga     3600
gcgagtgaca ttcgggacca gtctaggaac tggcttcctg gaccctgtta ccgccagcag     3660
cgagtatcaa agacatctgc ggataacaac aacagtgaat actcgtggac tggagctacc    3720
aagtaccacc tcaatggcag agactctctg gtgaatccgg gccggccat ggcaagccac     3780 aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080 catttcacc cctctccct catgggtgga ttcggactta acaccctcc tccacagatt       4140 ctcatcaaga caccccggt acctgcgaat ccttcgacca ccttcagtgc ggcaaagttt     4200
gcttccttca tcacacagta ctccacggga caggtcagcg tggagatcga gtgggagctg    4260
cagaaggaaa acagcaaacg ctggaatccc gaaattcagt acacttccaa ctacaacaag   4320
tctgttaatg tggactttac tgtggacact aatggcgtgt attcagagcc tcgcccatt      4380 ggcaccagat acctgactcg taatctgtaa ttgcttgtta atcaataaac cgtttaattc     4440
gtttcagttg aactttggtc tctgcgtatt tctttcttat ctagtttcca tggctacgta    4500
gataagtagc atggcgggtt aatcattaac tacaaggaac cctagtgat ggagttggcc      4560 actccctctc tgcgcgctcg ctcgctcact gaggccgggc gaccaaggt cgcccgacgc      4620 ccgggctttg cccgggcggc ctcagtgagc gagcgagcgc gcagagaggg agtggccaa     4679
```

<210> SEQ ID NO 2
<211> LENGTH: 1962
<212> TYPE: DNA
<213> ORGANISM: Homo sapiens

<400> SEQUENCE: 2

```
atggcggata ctctcccttc ggagtttgat gtgatcgtaa tagggacggg tttgcctgaa     60
tccatcattg cagctgcatg ttcaagaagt ggccggagag ttctgcatgt tgattcaaga    120
agctactatg gaggaaactg gccagtttt agcttttcag gactattgtc ctggctaaag    180
gaataccagg aaacagtga cattgtaagt gacagtccag tgtggcaaga ccagatcctt    240
gaaaatgaag aagccattgc tcttagcagg aaggacaaaa ctattcaaca tgtgaagta     300
ttttgttatg ccagtcagga tttgcatgaa gatgtcgaag aagctggtgc actgcagaaa    360
aatcatgctc ttgtgacatc tgcaaactcc acagaagctg cagattctgc cttcctgcct    420
acggaggatg agtcattaag cactatgagc tgtgaaatgc tcacagaaca aactccaagc    480
agcgatccag agaatgcgct agaagtaaat ggtgctgaag tgacagggga aaagaaaaac    540
cattgtgatg ataaaacttg tgtgccatca acttcagcag aagacatgag tgaaaatgtg    600
cctatagcag aagataccac agagcaacca aagaaaaaca gaattactta ctcacaaatt    660
attaagaag gcaggagatt taatattgat ttagtatcaa agctgctgta ttctcgagga    720
ttactaattg atcttctaat caaatctaat gttagtcgat atgcagagtt taaaaatatt    780
accaggattc ttgcatttcg agaaggacga gtggaacagg ttccgtgttc cagagcagat    840
gtctttaata gcaaacaact tactatggta gaaaagcgaa tgctaatgaa atttcttaca    900
ttttgtatgg aatatgagaa atatcctgat gaatataaag gatatgaaga atcacatttt    960
tatgaatatt taaagactca aaaattaacc cccaacctcc aatatattgt catgcattca   1020
attgcaatga catcagagac agccagcagc accatagatg gtctcaaagc taccaaaaac   1080
tttcttcact gtcttgggcg gtatggcaac actccatttt tgttccttt atatggccaa   1140
ggagaactcc cccagtgttt ctgcaggatg tgtgctgtgt tggtggaat ttattgtctt   1200
cgccattcag tacagtgcct tgtagtggac aaagaatcca gaaaatgtaa agcaattata   1260
gatcagtttg gtcagagaat aatctctgag catttcctcg tggaggacag ttactttcct   1320
gagaacatgt gctcacgtgt gcaatacagg cagatctcca gggcagtgct gattacagat   1380
agatctgtcc taaaaacaga ttcagatcaa cagatttcca ttttgacagt gccagcagag   1440
gaaccaggaa cttttgctgt tcgggtcatt gagttatgtt cttcaacgat gacatgcatg   1500
aaaggcacct atttggttca tttgacttgc acatcttcta aaacagcaag agaagattta   1560
gaatcagttg tgcagaaatt gtttgttcca tatactgaaa tggagataga aatgaacaa    1620
gtagaaaagc caagaattct gtgggctctt tacttcaata tgagagattc gtcagacatc   1680
agcaggagct gttataatga tttaccatcc aacgtttatg tctgctctgg cccagattgt   1740
ggtttaggaa atgataatgc agtcaaacag gctgaaacac ttttccagga atctgcccc    1800
aatgaagatt tctgtccccc tccaccaaat cctgaagaca ttatccttga tggagacagt   1860
ttacagccag aggcttcaga atccagtgcc ataccagagg ctaactcgga gactttcaag   1920
gaaagcacaa accttggaaa cctagaggag tcctctgaat aa                      1962
```

<210> SEQ ID NO 3
<211> LENGTH: 653
<212> TYPE: PRT
<213> ORGANISM: Homo sapiens

<400> SEQUENCE: 3

```
Met Ala Asp Thr Leu Pro Ser Glu Phe Asp Val Ile Val Ile Gly Thr
1               5                   10                  15
```

-continued

```
Gly Leu Pro Glu Ser Ile Ile Ala Ala Ala Cys Ser Arg Ser Gly Arg
             20                  25                  30

Arg Val Leu His Val Asp Ser Arg Ser Tyr Tyr Gly Gly Asn Trp Ala
         35                  40                  45

Ser Phe Ser Phe Ser Gly Leu Leu Ser Trp Leu Lys Glu Tyr Gln Glu
     50                  55                  60

Asn Ser Asp Ile Val Ser Asp Ser Pro Val Trp Gln Asp Gln Ile Leu
 65                  70                  75                  80

Glu Asn Glu Glu Ala Ile Ala Leu Ser Arg Lys Asp Lys Thr Ile Gln
                 85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
    130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser
            180                 185                 190

Ala Glu Asp Met Ser Glu Asn Val Pro Ile Ala Glu Asp Thr Thr Glu
        195                 200                 205

Gln Pro Lys Lys Asn Arg Ile Thr Tyr Ser Gln Ile Ile Lys Glu Gly
    210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
                245                 250                 255

Phe Lys Asn Ile Thr Arg Ile Leu Ala Phe Arg Glu Gly Arg Val Glu
            260                 265                 270

Gln Val Pro Cys Ser Arg Ala Asp Val Phe Asn Ser Lys Gln Leu Thr
        275                 280                 285

Met Val Glu Lys Arg Met Leu Met Lys Phe Leu Thr Phe Cys Met Glu
    290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
                325                 330                 335

Val Met His Ser Ile Ala Met Thr Ser Glu Thr Ala Ser Ser Thr Ile
            340                 345                 350

Asp Gly Leu Lys Ala Thr Lys Asn Phe Leu His Cys Leu Gly Arg Tyr
        355                 360                 365

Gly Asn Thr Pro Phe Leu Phe Pro Leu Tyr Gly Gln Gly Glu Leu Pro
    370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
                405                 410                 415

Lys Ala Ile Ile Asp Gln Phe Gly Gln Arg Ile Ile Ser Glu His Phe
            420                 425                 430

Leu Val Glu Asp Ser Tyr Phe Pro Glu Asn Met Cys Ser Arg Val Gln
```

```
               435                 440                 445
Tyr Arg Gln Ile Ser Arg Ala Val Leu Ile Thr Asp Arg Ser Val Leu
    450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
                485                 490                 495

Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
    610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650
```

<210> SEQ ID NO 4
<211> LENGTH: 1992
<212> TYPE: DNA
<213> ORGANISM: Homo sapiens

<400> SEQUENCE: 4

```
gatatcgaat tcctgcagcc cggcggcacc atggcggata ctctcccttc ggagtttgat      60
gtgatcgtaa tagggacggg tttgcctgaa tccatcattg cagctgcatg ttcaagaagt     120
ggccggagag ttctgcatgt tgattcaaga agctactatg aggaaactg ggccagtttt     180
agcttttcag gactattgtc ctggctaaag gaataccagg aaaacagtga cattgtaagt     240
gacagtccag tgtggcaaga ccagatcctt gaaaatgaag aagccattgc tcttagcagg     300
aaggacaaaa ctattcaaca tgtggaagta ttttgttatg ccagtcagga tttgcatgaa     360
gatgtcgaag aagctggtgc actgcagaaa atcatgctc ttgtgacatc tgcaaactcc     420
acagaagctg cagattctgc cttcctgcct acggaggatg agtcattaag cactatgagc     480
tgtgaaatgc tcacagaaca aactccaagc agcgatccag agaatgcgct agaagtaaat     540
ggtgctgaag tgacagggga aaagaaaac cattgtgatg ataaaacttg tgtgccatca     600
acttcagcag aagacatgag tgaaaatgtg cctatagcag aagataccac agagcaacca     660
aagaaaaaca gaattactta ctcacaaatt attaaagaag caggagatt taatattgat     720
ttagtatcaa agctgctgta ttctcgagga ttactaattg atcttctaat caaatctaat     780
gttagtcgat atgcagagtt taaaatatat accaggattc ttgcatttcg agaaggacga     840
gtggaacagg ttccgtgttc cagagcagat gtctttaata gcaaacaact tactatggta     900
```

-continued

| | |
|---|---|
| gaaaagcgaa tgctaatgaa atttcttaca ttttgtatgg aatatgagaa atatcctgat | 960 |
| gaatataaag gatatgaaga gatcacattt tatgaatatt taaagactca aaaattaacc | 1020 |
| cccaacctcc aatatattgt catgcattca attgcaatga catcagagac agccagcagc | 1080 |
| accatagatg gtctcaaagc taccaaaaac tttcttcact gtcttgggcg gtatggcaac | 1140 |
| actccatttt tgtttccttt atatggccaa ggagaactcc cccagtgttt ctgcaggatg | 1200 |
| tgtgctgtgt ttggtggaat ttattgtctt cgccattcag tacagtgcct tgtagtggac | 1260 |
| aaagaatcca gaaaatgtaa agcaattata gatcagtttg gtcagagaat aatctctgag | 1320 |
| catttcctcg tggaggacag ttactttcct gagaacatgt gctcacgtgt gcaatacagg | 1380 |
| cagatctcca gggcagtgct gattacagat agatctgtcc taaaaacaga ttcagatcaa | 1440 |
| cagatttcca ttttgacagt gccagcagag gaaccaggaa cttttgctgt tcgggtcatt | 1500 |
| gagttatgtt cttcaacgat gacatgcatg aaaggcacct atttggttca tttgacttgc | 1560 |
| acatcttcta aaacagcaag agaagattta gaatcagttg tgcagaaatt gtttgttcca | 1620 |
| tatactgaaa tggagataga aaatgaacaa gtagaaaagc caagaattct gtgggctctt | 1680 |
| tacttcaata tgagagattc gtcagacatc agcaggagct gttataatga tttaccatcc | 1740 |
| aacgtttatg tctgctctgg cccagattgt ggtttaggaa atgataatgc agtcaaacag | 1800 |
| gctgaaacac ttttccagga aatctgcccc aatgaagatt tctgtccccc tccaccaaat | 1860 |
| cctgaagaca ttatccttga tggagacagt ttacagccag aggcttcaga atccagtgcc | 1920 |
| ataccagagg ctaactcgga gactttcaag gaaagcacaa accttggaaa cctagaggag | 1980 |
| tcctctgaat aa | 1992 |

<210> SEQ ID NO 5
<211> LENGTH: 588
<212> TYPE: DNA
<213> ORGANISM: Woodchuck hepatitis B virus

<400> SEQUENCE: 5

| | |
|---|---|
| atcaacctct ggattacaaa atttgtgaaa gattgactgg tattcttaac tatgttgctc | 60 |
| cttttacgct atgtggatac gctgctttaa tgcctttgta tcatgctatt gcttcccgta | 120 |
| tggctttcat tttctcctcc ttgtataaat cctggttgct gtctctttat gaggagttgt | 180 |
| ggcccgttgt caggcaacgt ggcgtggtgt gcactgtgtt tgctgacgca accccactg | 240 |
| gttgggcat tgccaccacc tgtcagctcc tttccgggac tttcgctttc cccctcccta | 300 |
| ttgccacggc ggaactcatc gccgcctgcc ttgcccgctg ctggacaggg gctcggctgt | 360 |
| tgggcactga caattccgtg gtgttgtcgg ggaaatcatc gtccttcct tggctgctcg | 420 |
| cctgtgttgc cacctggatt ctgcgcggga cgtccttctg ctacgtccct tcggccctca | 480 |
| atccagcgga ccttccttcc gcggcctgc tgccggctct gcggcctctt ccgcgtcttc | 540 |
| gccttcgccc tcagacgagt cggatctccc tttgggccgc ctccccgc | 588 |

<210> SEQ ID NO 6
<211> LENGTH: 934
<212> TYPE: DNA
<213> ORGANISM: Gallus gallus

<400> SEQUENCE: 6

| | |
|---|---|
| attgacgtca ataatgacgt atgttcccat agtaacgcca ataggggactt tccattgacg | 60 |
| tcaatgggtg gagtatttac ggtaaactgc ccacttggca gtacatcaag tgtatcatat | 120 |
| gccaagtacg ccccctattg acgtcaatga cggtaaatgg cccgcctggc attatgccca | 180 |

```
gtacatgacc ttatgggact ttcctacttg gcagtacatc tacgtattag tcatcgctat      240
taccatggtc gaggtgagcc ccacgttctg cttcactctc cccatctccc ccccctcccc      300 accccccaatt ttgtatttat ttattttta attattttgt gcagcgatgg gggcggggggg     360 gggggggggg cgcgcgccag gcggggcggg gcggggcgag gggcggggcg gggcgaggcg      420
gagaggtgcg gcggcagcca atcagagcgg cgcgctccga aagtttcctt ttatggcgag      480
gcggcggcgc cggcggccct ataaaaagcg aagcgcgcgg cgggcgggag tcgctgcgcg      540
ctgccttcgc cccgtgcccc gctccgccgc cgcctcgcgc cgcccgcccc ggctctgact      600
gaccgcgtta ctcccacagg tgagcgggcg ggacggcccT tctcctccgg gctgtaatta      660
gcgcttggtt taatgacggc ttgtttcttt tctgtggctg cgtgaaagcc ttgaggggct      720
ccgggagggc cctttgtgcg ggggagcgg ctcggggctg tccgcggggg gacggctgcc      780 ttcgggggg acgggcagg gcggggttcg gcttctggcg tgtgaccggc ggctctagag       840
cctctgctaa ccatgttcat gccttcttct ttttcctaca gctcctgggc aacgtgctgg      900
ttattgtgct gtctcatcat tttggcaaag aatt                                  934

<210> SEQ ID NO 7
<211> LENGTH: 270
<212> TYPE: DNA
<213> ORGANISM: Bos primigenius

<400> SEQUENCE: 7
tcgctgatca gcctcgactg tgccttctag ttgccagcca tctgttgttt gccccctcccc     60 cgtgccttcc ttgaccctgg aaggtgccac tcccactgtc ctttcctaat aaaatgagga    120
aattgcatcg cattgtctga gtaggtgtca ttctattctg gggggtgggg tgggcagga    180 cagcaagggg gaggattggg aagacaatag caggcatgct ggggatgcgg tgggctctat    240
ggcttctgag gcggaaagaa ccagctgggg                                      270

<210> SEQ ID NO 8
<211> LENGTH: 144
<212> TYPE: DNA
<213> ORGANISM: adeno-associated virus 2

<400> SEQUENCE: 8
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gatt                                            144

<210> SEQ ID NO 9
<211> LENGTH: 145
<212> TYPE: DNA
<213> ORGANISM: adeno-associated virus 2

<400> SEQUENCE: 9
tgcgcgctcg ctcgctcact gaggccgggc gaccaaaggt cgcccgacgc ccgggctttg      60
cccgggcggc ctcagtgagc gagcgagcgc gcagagcttt ttgcaaaagc ctaggcctcc    120
aaaaaagcct cctcactact tctgg                                           145
```

AAV-VECTORS FOR USE IN GENE THERAPY OF CHOROIDEREMIA

This application is a national phase filing under 35 USC §371 of PCT Application No. PCT/GB2012/050376 entitled "AAV-VECTORS FOR USE IN GENE THERAPY OF CHOROIDEREMIA", filed Feb. 21, 2012 which claims priority to Patent Application GB 1103062.4 filed Feb. 22, 2011 both of which, and the specification and claims thereof, are incorporated herein by reference.

FIELD OF THE INVENTION

The present invention relates to gene therapy for treatment or prevention of choroideremia.

BACKGROUND OF THE INVENTION

Choroideremia is a rare X-linked progressive degeneration of the choroid, retinal pigment epithelium and photoreceptors of the eye. The typical natural history in afflicted males is onset of nightblindness during teenage years, and then progressive loss of peripheral vision during the 20's and 30's leading to complete blindness in the 40's. Female carriers have mild symptoms most notably nightblindness but may occasionally have a more severe phenotype.

The disease is caused by mutations in the REP1 gene, (Rab escort protein 1), which is located on the X chromosome 21q region. In most cells in the body, the REP2 protein, which is 75% homologous to REP1, compensates for the REP1 deficiency. In the eye, however, for reasons that are not yet clear, REP2 is unable to compensate for the REP1 deficiency. Hence in the eye, REP polypeptide activity is insufficient to maintain normal prenylation of the target proteins (Rab GTPases) leading to cellular dysfunction and ultimate death, primarily affecting the outer retina and choroid.

There is no treatment for choroideremia, and there is a lack of models to assess therapeutic strategies. There is a need for provision of such a therapy.

SUMMARY OF THE INVENTION

The present invention relates to a vector which can be used for gene therapy of choroideremia, and methods of preventing or treating this disease using the vector. The invention also relates to the use of the vector in methods of preventing or treating choroideremia.

The vector of the invention is a viral vector, specifically based on the genome of adeno-associated virus (AAV). The vector comprises a sequence which encodes REP1 or a variant thereof, thus allowing for the expression of REP1 function in a target cell. The methods and uses of the invention specifically involve the administration of the vector to a patient by direct retinal, subretinal or intravitreal injection to treat or prevent choroideremia.

Accordingly, the invention provides a vector, which comprises an adeno-associated virus (AAV) genome or a derivative thereof and a polynucleotide sequence encoding REP1 or a variant thereof. The invention further provides a method of treating or preventing choroideremia in a patient in need thereof, comprising administering a therapeutically effective amount of a vector according to any one of the preceding claims to said patient by direct retinal, subretinal or intravitreal injection, and thereby treating or preventing choroideremia in said patient. The invention additionally provides a vector of the invention for use in a method of treating or preventing choroideremia by administering said vector to a patient by direct retinal, subretinal or intravitreal injection.

Western blots are shown in the left panels for REP1 (top panel) and alpha-tubulin (bottom panel) as a loading control. Lane 1: 40 µg cell lysate from control wildtype (WT) fibroblasts. Lane 2: 40 µg cell lysate from Chm fibroblasts. Lanes 3-6: 40, 20, 10 and 5 µg cell lysate from Chm fibroblasts transduced with AAV2.REP1 vector. Lane 7: human REP1 recombinant protein. Since the 5 µg lysate hREP1 band has a similar density to 40 µg of the WT fibroblast lysate, the level of hREP1 achieved with the AAV2.REP1 vector can achieve at least 8 times (40/5) the normal wild type levels under these conditions.

As a positive control for the promoter and other non-REP1 sequences in this assay, results from a control AAV vector expressing green fluorescent protein (GFP) in place of REP1 (AAV-CAG-GFP) are also shown.

Western blots are shown in the right panels for GFP (top panel) and alpha-tubulin (bottom panel) as a loading control. Lane 1: 40 µg cell lysate from wildtype (WT) fibroblasts. Lane 2: 40 µg cell lysate from Chm fibroblasts transduced with AAV2.GFP vector (AAV-CAG-REP1). The high levels of GFP shown confirm the efficiency of this vector expression cassette in transducing human cells that are deficient of REP1 activity, as would be the case in patients with choroideremia.

Figure 1:
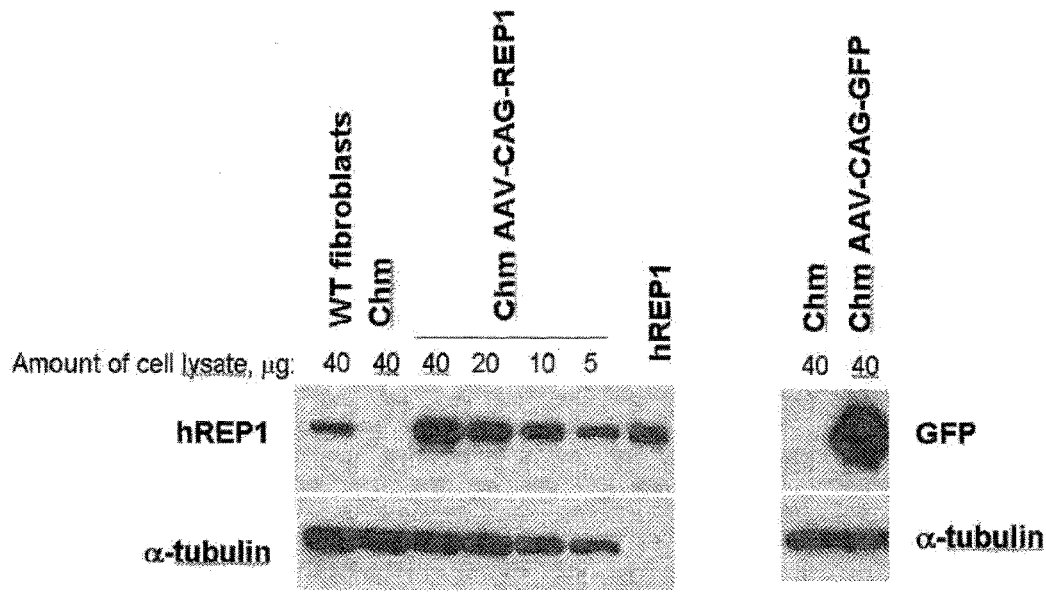
FIG. 1 shows that the AAV.REP1 (AAV-CAG-REP1) vector can transduce human fibroblasts isolated from a patient with choroideremia (Chm) efficiently. The relative levels of expression of human REP1 protein (hREP1) are compared by Western blot, allowing quantification of AAV2.REP1 vector activity by comparing the amount of hREP1 in different concentrations of cell lysate. With regard to the labelling, CAG is the Chicken beta Actin with CMV enhancer promoter sequence—interchangeably referred to as 'CBA' in various publications and parts of this document.
Figure 2:
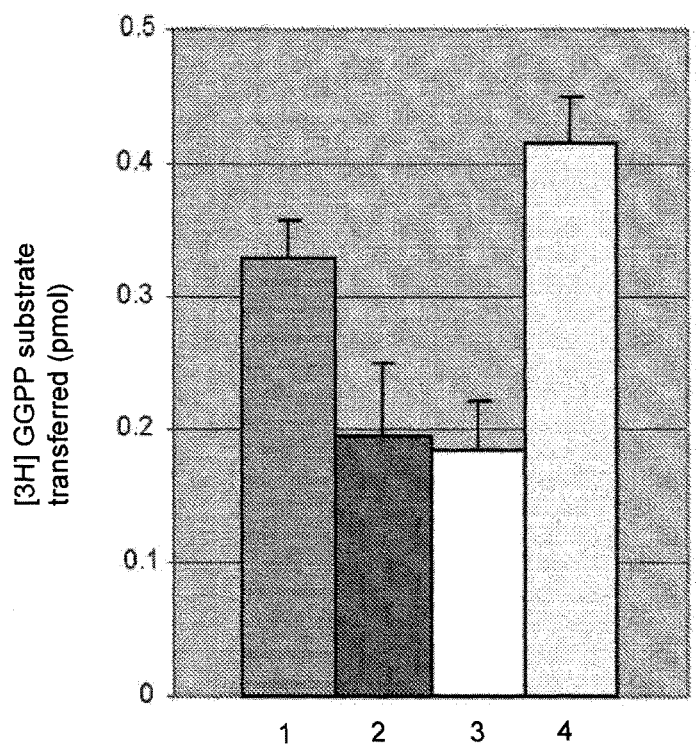

FIG. 2 shows an assessment of prenylation activity in WT human fibroblasts (first column on left—light grey), Chm fibroblasts (second column 13 dark grey), AAV-CAG-GFP vector-transduced Chm fibroblasts (third column—white, negative control) and AAV-CAG-REP1 transduced Chm fibroblasts (fourth column—white). The y axis shows the amount of radioactively labelled substrate [3H] GGPP substrate transferred in pmol, which is a measure of prenylation, the function of REP1. Columns show error bars as standard deviations (n=4 for each column). Levels of [3H]-GGPP were measured in 10 mg of protein extract. The cyan column fourth from left confirms that the function of prenylation is also restored to wild type levels and beyond, following transduction with the AAV.REP1 vector. This confirms that the REP1 protein detected by Western blot in FIG. 1 has the predicted function.

Figure 3:
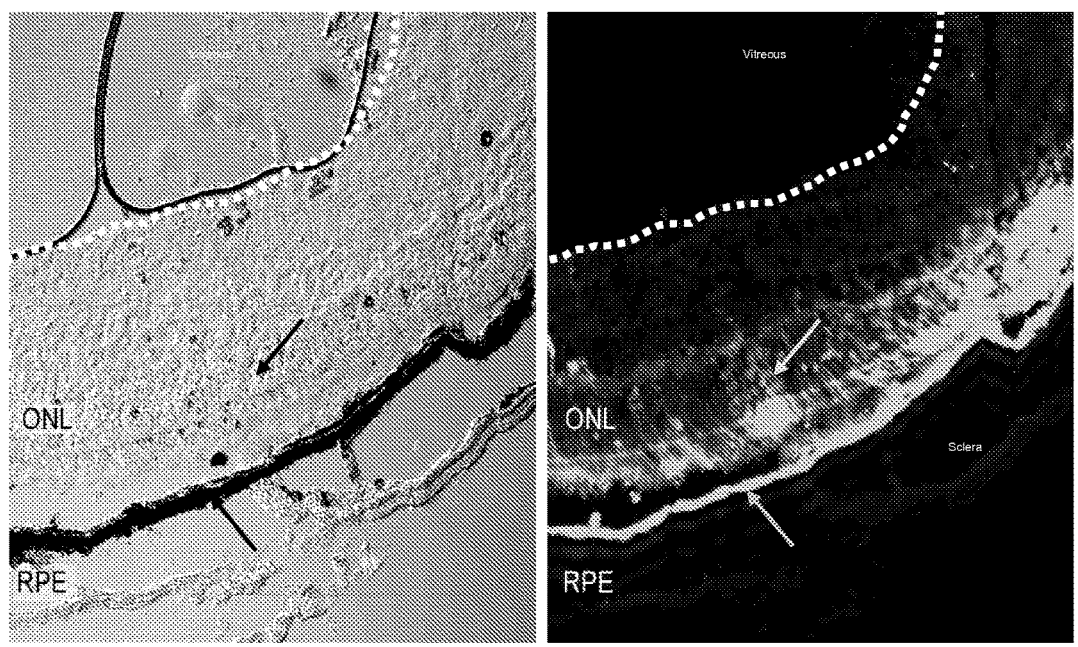

FIG. 3 shows that the AAV vector has the correct tropism for cells of the outer retina (photoreceptors and choroid) following subretinal injection in a mouse model. The right panel shows appropriate expression of a green fluorescent protein (GFP) marker (arrows) in the photoreceptors of the outer nuclear layer (ONL) and retinal pigment epithelium (RPE) following subretinal injection of the AAV2.CBA.GFP.WPRE.BGH vector in the mouse eye. Left panel shows greyscale of same image. This confirms that the AAV2.CBA.WPRE.BGH regulatory sequences are capable of highly efficient transgene expression in the retinal cells that need to be targeted in patients with choroideremia.

Figure 4:
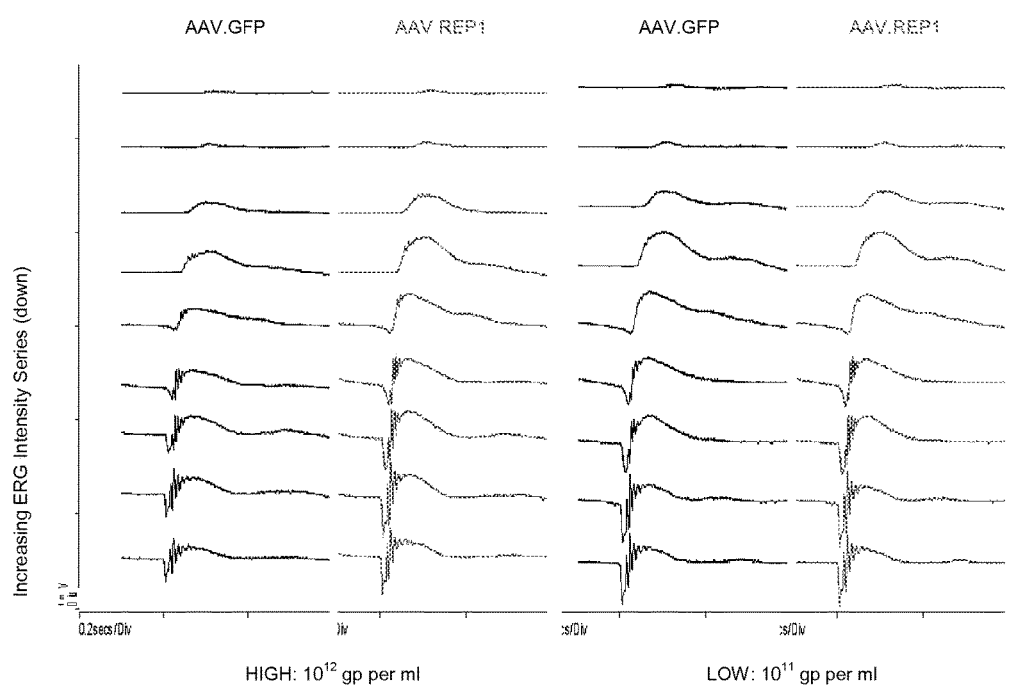

FIG. 4 shows that the AAV.REP1 vector does not adversely affect outer retinal function at high doses in the mouse retina. The results of a toxicity study with measurement of an electroretinogram (ERG) six months after subretinal injection of 2×1 microliter of either high (n=5) or low (n=4) doses of AAV.REP1 vector into the mouse subretinal space are shown. Low dose=$1\times10^{11}$ and high dose=$1\times10^{12}$ genome particles (gp) per ml (the starting dose for human clinical trials is $1\times10^{11}$ gp per ml). The AAV.GFP vector has an identical expression cassette and is also diluted to the same dose prior to injection to act as a control. The Y axis shows the ERG trace at increasing flash intensities ranging from scotopic (dark adapted) rod responses above to bright to photopic responses below (which would also include cone photoreceptors). The traces at all points show similar ERG amplitudes following both high and low dose AAV.REP1 exposure. In the high dose group the equivalent GFP amplitudes are slightly reduced, in keeping with the known marginal effect on retinal function of GFP at high levels. This GFP effect also acts as a positive control to confirm the sensitivity of this test.

DESCRIPTION OF SEQUENCES

SEQ ID NO: 1 is a DNA sequence for the AAV2 genome.

SEQ ID NO: 2 is a DNA sequence encoding the human Rep-1 protein, transcript variant 1.

SEQ ID NO: 3 is an amino acid sequence for the human Rep-1 protein, transcript variant 1.

SEQ ID NO: 4 is a DNA sequence encoding the human Rep-1 protein, transcript variant 1, which includes a portion of the 5'UTR.

SEQ ID NO: 5 is a DNA sequence for the woodchuck hepatitis postregulatory element (WPRE).

SEQ ID NO: 6 is a DNA sequence for a chicken beta actin (CBA) promoter.

SEQ ID NO: 7 is a DNA sequence for a polyadenylation site from Bovine Growth Hormone (bGH polyA).

SEQ ID NO: 8 is a DNA sequence for a 5'inverted terminal repeat (ITR) of AAV2.

SEQ ID NO: 9 is a DNA sequence for a 3'ITR of AAV2.

DETAILED DESCRIPTION OF THE INVENTION

The present invention provides a therapy for choroideremia. This is based on a gene therapy approach to the disease utilising a genetic construct to deliver a transgene to restore REP1 function. The genetic construct is a vector based on an adeno-associated virus (AAV) genome which comprises a polynucleotide sequence encoding REP1 or a variant thereof. This polynucleotide sequence is also referred to herein as the "transgene". The present inventors established a model for evaluating strategies for treatment of choroideremia and surprisingly demonstrate use of a vector of the invention to target the cellular dysfunction underlying the disease.

Vector

AAV Genome

The vector of the invention comprises firstly an adeno-associated virus (AAV) genome or a derivative thereof.

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly, the AAV genome of the vector of the invention is typically replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or Glade of AAV. Thus, the AAV genome may be the full genome of a naturally occurring AAV virus. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10 and AAV11, also recombinant serotypes, such as Rec2 and Rec3, recently identified from primate brain.

A preferred serotype of AAV for use in the invention is AAV2. An AAV2 genome may have the sequence of SEQ ID NO: 1. Other serotypes of particular interest for use in the invention include AAV4, AAV5 and AAV8 which efficiently transduce tissue in the eye, such as the retinal pigmented epithelium. The serotype of AAV which is used can be an AAV serotype which is not AAV4. Reviews of AAV serotypes may be found in Choi et al (Curr Gene Ther. 2005; 5(3); 299-310) and Wu et al (*Molecular Therapy.* 2006; 14(3), 316-327). The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include: Clade A: AAV1 NC_002077, AF063497, AAV6 NC_001862, Hu. 48 AY530611, Hu 43 AY530606, Hu 44 AY530607, Hu 46 AY530609

Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29

AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377,

Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623

Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013

Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu17 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556

Clade F: Hu14 (AAV9) AY530579, Hu31 AY530596, Hu32 AY530597, Clonal Isolate AAV5 Y18065, AF085716, AAV 3 NC_001729, AAV 3B NC_001863, AAV4 NC_001829, Rh34 AY243001, Rh33 AY243002, Rh32 AY243003/

The skilled person can select an appropriate serotype, Glade, clone or isolate of AAV for use in the present invention on the basis of their common general knowledge. For instance, the AAV5 capsid has been shown to transduce primate cone photoreceptors efficiently as evidenced by the successful correction of an inherited color vision defect (Mancuso et al., Nature 2009, 461:784-7).

It should be understood however that the invention also encompasses use of an AAV genome of other serotypes that may not yet have been identified or characterised. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cells within the degenerating retina in choroideremia. Thus, preferred AAV serotypes for use in AAV viruses administered to patients are ones which infect cells of the neurosensory retina and retinal pigment epithelium.

Typically, the AAV genome of a naturally derived serotype or isolate or Glade of AAV comprises at least one inverted terminal repeat sequence (ITR). An ITR sequence acts in cis to provide a functional origin of replication, and allows for integration and excision of the vector from the genome of a cell. In preferred embodiments, one or more ITR sequences flank the polynucleotide sequence encoding Rep-1 or a variant thereof. Preferred ITR sequences are those of AAV2, including those of SEQ ID NOs 8 and 9 and variants thereof. The AAV genome typically also comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

A promoter will be operably linked to each of the packaging genes. Specific examples of such promoters include the p5, p19 and p40 promoters (Laughlin et al., 1979, PNAS, 76:5567-5571). For example, the p5 and p19 promoters are generally used to express the rep gene, while the p40 promoter is generally used to express the cap gene.

As discussed above, the AAV genome used in the vector of the invention may therefore be the full genome of a naturally occurring AAV virus. For example, a vector comprising a full AAV genome may be used to prepare AAV virus in vitro. However, while such a vector may in principle be administered to patients, this will be done rarely in practice. Preferably the AAV genome will be derivatised for the purpose of administration to patients. Such derivatisation is standard in the art and the present invention encompasses the use of any known derivative of an AAV genome, and derivatives which could be generated by applying techniques known in the art. Derivatisation of the AAV genome and of the AAV capsid are reviewed in Coura and Nardi (*Virology Journal*, 2007, 4:99), and in Choi et al and Wu et al, referenced above.

Derivatives of an AAV genome include any truncated or modified forms of an AAV genome which allow for expression of a Rep-1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs will preferably flank the polynucleotide sequence encoding REP1 or a variant thereof at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome of SEQ ID NO: 1, the following portions could therefore be removed in a derivative of the invention: One inverted terminal repeat (ITR) sequence, the replication (rep) and capsid (cap) genes (NB: the rep gene in the wildtype AAV genome should not to be confused with REP1, the human gene affected in choroideremia). However, in some embodiments, including in vitro embodiments, derivatives may additionally include one or more rep and/or cap genes or other viral sequences of an AAV genome. Naturally occurring AAV virus integrates with a high frequency at a specific site on human chromosome 19, and shows a negligible frequency of random integration, such that retention of an integrative capacity in the vector may be tolerated in a therapeutic setting.

Where a derivative genome comprises genes encoding capsid proteins i.e. VP1, VP2 and/or VP3, the derivative may be a chimeric, shuffled or capsid-modified derivative of one or more naturally occurring AAV viruses. In particular, the invention encompasses the provision of capsid protein sequences from different serotypes, clades, clones, or isolates of AAV within the same vector i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are cotransfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al., 2008 ARVO Abstract: D1048). The unrelated protein may also be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al, referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a polynucleotide sequence comprising an AAV genome or derivative thereof and a sequence encoding REP1 or a variant thereof.

For the avoidance of doubt, the invention also provides an AAV viral particle comprising a vector of the invention. The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The invention additionally provides a host cell comprising a vector or AAV viral particle of the invention.

REP1

The vector of the invention further comprises a polynucleotide sequence encoding a REP1 polypeptide or a variant thereof. The human cDNA sequence for REP1 (or Rab escort protein-1, also known as Rab protein geranylgeranyltransferase component A) is shown in SEQ ID NO: 2 and encodes the protein shown in SEQ ID NO: 3. A further cDNA sequence for REP1 is shown in SEQ ID NO: 4.

A REP1 polypeptide or variant thereof is any polypeptide which assists in prenylation of a Rab GTPase protein. The ability of a REP1 polypeptide or variant thereof to assist in prenylation of a Rab GTPase protein can be routinely determined by a person skilled in the art. A polynucleotide sequence encoding a variant of REP1 is any sequence which encodes a protein assisting in prenylation activity for a Rab-1 GTPase. Preferably the sequence encodes a protein which assists in providing similar or higher prenylation activity for Rab-1 GTPase compared to the polypeptide of SEQ ID NO: 3.

More preferably, the polynucleotide sequence encodes SEQ ID NO: 3 or a variant thereof, and is a variant of the polynucleotide sequence of SEQ ID NO: 2. A variant of SEQ ID NO: 2 or 3 may comprise truncations, mutants or homologues thereof, and any transcript variants thereof which encode a functional REP polypeptide.

Any homologues mentioned herein are typically at least 70% homologous to a relevant region of SEQ ID NO: 2 or 3. A specific homologue is the REP2 polypeptide, which is 75% homologous to REP1, and can functionally compensate for REP1 deficiency.

Homology can be measured using known methods. For example the UWGCG Package provides the BESTFIT program which can be used to calculate homology (for example used on its default settings) (Devereux et at (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et at (1990) J Mol Biol 215:403-10. Software for performing BLAST analyses is publicly available through the National Center for Biotechnology Information (http://www.ncbi.nlm.nih.gov/).

In preferred embodiments, a variant sequence may encode a polypeptide which is at least 55%, 65%, 70%, 75%, 80%, 85%, 90% and more preferably at least 95%, 97% or 99% homologous to a relevant region of SEQ ID NO: 3 over at least 20, preferably at least 30, for instance at least 40, 60, 100, 200, 300, 400 or more contiguous amino acids, or even over the entire sequence of the variant. The relevant region will be one which provides for functional activity of REP1 in assisting in prenylation activity for a Rab-1 GTPase.

Alternatively, and preferably the variant sequence may encode a polypeptide having at least 70%, 75%, 80%, 85%, 90% and more preferably at least 95%, 97% or 99% homologous to full-length SEQ ID NO: 3 over its entire sequence. Typically the variant sequence differs from the relevant region of SEQ ID NO: 3 by at least, or less than, 2, 5, 10, 20, 40, 50 or 60 mutations (each of which can be substitutions, insertions or deletions).

A variant Rep-1 polypeptide may have a percentage identity with a particular region of SEQ ID NO: 3 which is the same as any of the specific percentage homology values (i.e. it may have at least 70%, 80% or 90% and more preferably at least 95%, 97% or 99% identity) across any of the lengths of sequence mentioned above.

Variants of SEQ ID NO: 3 also include truncations. Any truncation may be used so long as the variant is still able to prenylate a Rab-1 GTPase substrate polypeptide. Truncations will typically be made to remove sequences that are non-essential for prenylation activity and/or do not affect conformation of the folded protein, in particular folding of the active site. Appropriate truncations can routinely be identified by systematic truncation of sequences of varying length from the N- or C-terminus. Preferred truncations are N-terminal and may remove all other sequences except for the catalytic domain.

Variants of SEQ ID NO: 3 further include mutants which have one or more, for example, 2, 3, 4, 5 to 10, 10 to 20, 20 to 40 or more, amino acid insertions, substitutions or deletions with respect to a particular region of SEQ ID NO: 3. Deletions and insertions are made preferably outside of the catalytic domain as described below. Substitutions are also typically made in regions that are non-essential for protease activity and/or do not affect conformation of the folded protein.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the 20 main amino acids as defined in Table A below.

Similarly, preferred variants of the polynucleotide sequence of SEQ ID NO: 2 include polynucleotides having at least 70%, 75%, 80%, 85%, 90% and more preferably at least 95%, 97% or 99% homologous to a relevant region of SEQ ID NO: 2. Preferably the variant displays these levels of homology to full-length SEQ ID NO: 2 over its entire sequence

TABLE A

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Promoters and Regulatory Sequences

The vector of the invention also includes elements allowing for the expression of the REP1 transgene in vitro or in vivo. Thus, the vector typically comprises a promoter sequence operably linked to the polynucleotide sequence encoding Rep-1 or a variant thereof.

Any suitable promoter may be used. The promoter sequence may be constitutively active i.e. operational in any host cell background, or alternatively may be active only in a specific host cell environment, thus allowing for targeted expression of the transgene in a particular cell type. The promoter may show inducible expression in response to presence of another factor, for example a factor present in a host cell. In any event, where the vector is administered for therapy, the promoter must be functional in a retinal cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters for the Rep-1 transgene include the chicken beta-actin (CBA) promoter, optionally in combination with a cytomegalovirus (CME) enhancer element. A particularly preferred promoter is a hybrid CBA/CAG promoter, for example the promoter used in the rAVE expression cassette (GeneDetect.com). A further preferred promoter is shown in SEQ ID NO: 6. Examples of promoters based on human sequences that would induce retina specific gene expression include rhodospin kinase for rods and cones (Allocca et al., 2007, J Viol 81:11372-80), PR2.1 for cones only (Mancuso et al. 2009, Nature) and/or RPE65 for the retinal pigment epithelium (Bainbridge et al., 2008, N Eng J Med).

The vector of the invention may also comprise one or more additional regulatory sequences with may act pre- or post-transcriptionally. The regulatory sequence may be part of the native REP1 gene locus or may be a heterologous regulatory sequence. The vector of the invention may comprise portions of the 5'UTR or 3'UTR from the native REP1 transcript. For example, the polynucleotide of SEQ ID NO:4 includes some of the 5'UTR sequence from the native REP1 transcript.

Regulatory sequences are any sequences which facilitate expression of the transgene i.e. act to increase expression of a transcript, improve nuclear export of mRNA or enhance its stability. Such regulatory sequences include for example enhancer elements, postregulatory elements and polyadenylation sites. A preferred polyadenylation site is the Bovine Growth Hormone poly-A signal which may be as shown in SEQ ID NO: 7. In the context of the vector of the invention such regulatory sequences will be cis-acting. However, the invention also encompasses the use of trans-acting regulatory sequences located on additional genetic constructs.

A preferred postregulatory element for use in a vector of the invention is the woodchuck hepatitis postregulatory element (WPRE) or a variant thereof. The sequence of the WPRE is provided in SEQ ID NO:5. The invention encompasses the use of any variant sequence of the WPRE which increases expression of the REP1 transgene compared to a vector without a WPRE. Preferably, variant sequences display at least 70% homology to SEQ ID NO:5 over its entire sequence, more preferably 75%, 80%, 85%, 90% and more preferably at least 95%, 97% or 99% homology to SEQ ID NO: 5 over its entire sequence.

Another regulatory sequence which may be used in a vector of the present invention is a scaffold-attachment region (SAR). Additional regulatory sequences may be selected by the skilled person on the basis of their common general knowledge.

Preparation of Vector

The vector of the invention may be prepared by standard means known in the art for provision of vectors for gene therapy. Thus, well established public domain transfection, packaging and purification methods can be used to prepare a suitable vector preparation.

As discussed above, a vector of the invention may comprise the full genome of a naturally occurring AAV virus in addition to a polynucleotide sequence encoding REP1 or a variant thereof. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with AAV5 or AAV8 capsid proteins. This packaged viral vector typically comprises one or more AAV2 ITRs optionally as shown in SEQ ID NO: 8 and/or 9, or variants thereof.

As mentioned above, AAV viruses are replication incompetent and so helper virus functions, preferably adenovirus helper functions will typically also be provided on one or more additional constructs to allow for AAV replication.

All of the above additional constructs may be provided as plasmids or other episomal elements in the host cell, or alternatively one or more constructs may be integrated into the genome of the host cell.

In these aspects, the invention provides a method for production of a vector of the invention. The method comprises providing a vector which comprises an adeno-associated virus (AAV) genome or a derivative thereof and a polynucleotide sequence encoding REP1 or a variant thereof in a host cell, and providing means for replication and assembly of said vector into an AAV viral particle. Preferably, the method comprises providing a vector comprising a derivative of an AAV genome and a polynucleotide sequence encoding REP1 or a variant thereof, together with one or more additional genetic constructs encoding AAV and/or helper virus functions. Typically, the derivative of an AAV genome comprises at least one ITR. Optionally, the method further comprises a step of purifying the assembled viral particles. Additionally, the method may comprise a step of formulating the viral particles for therapeutic use.

Methods of Therapy and Medical Uses

As discussed above, the present inventors have surprisingly demonstrated that a vector of the invention may be used to address the cellular dysfunction underlying choroideremia. In particular, they have shown that use of the vector can correct the prenylation defect associated with choroideremia. This provides a means whereby the degenerative process of the disease can be treated, arrested, palliated or prevented.

The invention therefore provides a method of treating or preventing choroideremia in a patient in need thereof, comprising administering a therapeutically effective amount of a vector of the invention to the patient by direct retinal, subretinal or intravitreal injection. Accordingly, choroideremia is thereby treated or prevented in said patient.

In a related aspect, the invention provides for use of a vector of the invention in a method of treating or preventing choroideremia by administering said vector to a patient by direct retinal, subretinal or intravitreal injection. Additionally, the invention provides the use of a vector of the invention in the manufacture of a medicament for treating or preventing choroideremia by direct retinal, subretinal or intravitreal injection.

In all these embodiments, the vector of the invention may be administered in order to prevent the onset of one or more symptoms of choroideremia. The patient may be asymptomatic. The subject may have a predisposition to the disease. The method or use may comprise a step of identifying whether or not a subject is at risk of developing, or has, choroideremia. A prophylactically effective amount of the vector is administered to such a subject. A prophylactically effective amount is an amount which prevents the onset of one or more symptoms of the disease.

Alternatively, the vector may be administered once the symptoms of the disease have appeared in a subject i.e. to cure existing symptoms of the disease. A therapeutically effective amount of the antagonist is administered to such a subject. A therapeutically effective amount is an amount which is effective to ameliorate one or more symptoms of the disease. Typically, such an amount increases the level of prenylation of Rab GTPases in the eye. This can be confirmed as described below. Such an amount may also arrest, slow or reverse some loss of peripheral vision associated with choroideremia. Such an amount may also arrest, slow or reverse onset of nightblindness.

The subject may be male or female. Male subjects show more severe symptoms, since choroideremia is an X-linked disease, but female subjects also display symptoms of the disease and occasionally have a severe phenotype. The subject is preferably identified as being at risk of, or having, the disease. The retina may show the characteristic appearance initially of thinning of the choroid and progressing to exposure of the underlying sclera in patches. There may be loss of amplitude of the electroretinogram peripherally. In many cases there may be a family history of choroideremia. Usually, but not always, a mutation may be identified in the REP1 gene located on the X-chromosome.

The administration of the vector is typically by direct retinal or subretinal injection. This includes direct delivery to cells of the neurosensory retina and retinal pigment epithelium, such as epithelial or photoreceptor cells. The delivery is made typically directly to or subretinally to the degenerating retina in a choroideremia patient. The vector may transduce the above target cells without entering any other cell populations. Intravitreal injection may also be used to deliver the vector of the invention. The delivery may not be subretinal or may not be by subretinal injection. The delivery may not be transvitreal.

The dose of a vector of the invention may be determined according to various parameters, especially according to the age, weight and condition of the patient to be treated; the route of administration; and the required regimen. Again, a physician will be able to determine the required route of administration and dosage for any particular patient.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where vector may not have targeted the correct region of retina for whatever reason (such as surgical complication). The treatment is preferably a single permanent treatment for each eye, but repeat injections, for example in future years and/or with different AAV serotypes may be considered.

The invention also provides a method of monitoring treatment or prevention of choroideremia in a patient comprising measuring prenylation activity ex vivo in retinal cells obtained from said patient following administration of the AAV vector of the invention by direct retinal, subretinal or intravitreal injection. This method allows for determination of the efficacy of treatment.

Pharmaceutical Compositions

The vector of the invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

EXAMPLES

The present Examples describe a model for testing therapeutic strategies for choroideremia and correction of the disease phenotype. Genetic constructs, consisting of a promoter, the REP1 cDNA, and 3' regulatory elements, when packaged into a recombinant viral vector, are shown to efficiently transduce target cells within the degenerating retina.

Example 1

Cloning of Human REP1 cDNA, and Generation of the CBA-REP-1-WPRE Expression Cassette, Construction of pAAV-CBA-REP-1-WPRE-bGHpA and Packaging of AAV REP-1 Virus A cDNA of human REP1 was isolated from a human cDNA library using PCR amplification and primers homologous to the known REP1 sequence The cDNA isolated was sequenced and shown to be homologous to the known translated Variant 1 of the REP1 mRNA sequence as deposited into Genbank, Accession Number NM_000390. The cDNA has the sequence of SEQ ID NO: 4.

This cDNA was inserted into a pAAV cis plasmid, termed pAM. pAM is a high copy number plasmid originally derived from pBR322, but includes stabilized AAV-2 left and right inverted terminal repeats which flank the expression cassette of choice. For the AAV-REP1 vector, a modified CBA/CAG promoter (chicken beta-actin with CMV enhancer) was used to drive expression of REP1 and a modified WPRE sequence and bGH polyA were provided 3' to the cDNA. This plasmid was termed pAAV2-CBA-hREP-1-WPRE-bGH, (pAAV-REP-1).

pAAV-REP-1 was used to generate recombinant AAV-Rep-1 using well established and public domain triple transfection packaging and purification methods Vector stocks generated using this method varied in genomic titer,

Example 2

Expression of REP1 from Vector in Human Choroideraemia (Chm) Cells

Expression of REP1 from the AAV2 REP1 vector was evaluated in human choroideremia (Chm) fibroblasts. These fibroblast cells were obtained with ethical consent from a skin biopsy taken from a choroideraemia patient. Expression of GFP from a control vector served as a control. As a prelude to the work with human cells, expression was also confirmed after subretinal injection of the AAV.REP1 vector in mice by Western blot, as the antibody probe recognises the human but not mouse forms of REP1 protein.

Results are shown in FIG. 1. REP1 was not detected by immunoblotting with an anti-hREP1 antibody in nontransduced Chm fibroblasts (lane 2), whereas REP1 is detected in normal (WT=human wildtype) fibroblasts (lane 1). Following transduction with the AAV2.REP1 vector, at equal doses of 40 μg of lysate and dilution to 5 μg it can be seen that the level of hREP1 expressed by the AAV2.REP1 vector in Chm cells is approximately ten fold higher (lanes 3-6) than the levels in wildtype cells (lane 1). No toxic effects on cell growth were observed with this degree of over-expression.

Example 3

Correction of Prenylation Defect by Vector in Chm Cells

Choroideraemia mice do not have a retinal degeneration phenotype in the same way as human patients so it is not possible to perform a direct assessment of retinal rescue using a gene therapy approach. For this reason, correction of the disease phenotype was assessed in human Chm cells in vitro.

Results are shown in FIG. 2. Transduction with the AAV2.REP1 showed a correction of the prenylation defect seen in Chm cells, raising the prenylation activity to significantly higher than normal levels after treatment of $2 \times 10^5$ cells with $1.5 \times 10^{10}$ viral genome particles of AAV2.REP1. This confirms that the AAV2.REP1 vector expresses functional REP1 protein in human cells affected by choroideraemia.

In more detail, the normal prenylation activity in wildtype (WT) fibroblasts yields approximately 0.32 pmol of [3H]-GGPP; in choroideremia (Chm) fibroblasts this is reduced to 0.19 pmol. As expected the prenylation activity was unchanged following transduction of the Chm fibroblasts with the AAV.GFP control vector. Following transduction with the AAV2.REP1 vector, however, the prenylation activity increased significantly to yield 0.42 pmol of [3H]-GGPP (n=4, p<0.01).

Example 4

Targeted In Vivo Expression of Reporter Gene from Vector in Mice

To confirm the ubiquitous activity of the CBA promoter and regulatory sequences in the AAV2 vector, the gene encoding REP1 was replaced with a reporter gene encoding green fluorescent protein (GFP) to create AAV2.CBA.GFP.WPRE.BGH (AAV2.GFP). GFP was selected to evaluate in vivo expression, since although easy to identify on Western blots, the human REP1 protein is not easily detected by indirect immunohistochemistry on retinal sections.

The AAV2.GFP construct was injected into the mouse subretinal space and expression of GFP was monitored by microscopy. Results are shown in FIG. 3, which confirm that the vector had the predicted tropism for both the neurosensory retina and retinal pigment epithelium. This confirms the capsid sequence and regulatory elements lead to high levels of gene expression in photoreceptors and the retinal pigment epithelium.

Example 5

Toxicity Study

Doses of AAV2.REP1 vector were injected into the subretinal space of wild-type mice (n=9) in order to determine any possible toxic effects in retinal function at the very highest doses. We tested vector concentrations in mice ($1 \times 10^{11}$ and $1 \times 10^{12}$ gp per ml) that were a log unit higher than proposed high and low concentrations to be used in patients ($10^{10}$ and $10^{11}$ gp per ml).

Results are shown in FIG. 4. No toxic effects on the electroretinogram (ERG) were detected six months after subretinal injection with either the high (n=5) or low (n=4) dose of AAV.REP1 vector. To control for any non-specific effects of retinal surgery or the AAV2 vector, the fellow eye had a very similar subretinal injection and titre of AAV2.GFP.

At the highest AAV2.GFP dose there was a mild reduction in the ERG amplitude, which reflects a mild known toxic effect using the maximal dose of vector expressing GFP with this strong promoter, and confirms the sensitivity of this test in detecting a dose-related effect. Nevertheless there was no detectable ERG reduction in AAV2.REP1 treated eyes at either dose which suggested that REP1 over-expression in the retina was less toxic than GFP.

---

What is claimed is:

1. A method of treating a human subject suffering from choroideremia, the method comprising: administering by subretinal injection a therapeutically effective amount of an AAV2 vector particle comprising a polynucleotide encoding a Rab escort protein 1 (REP1) having at least 97% sequence identity with SEQ ID NO: 3, wherein said polynucleotide is operably linked to a promoter, wherein one or more retinal pigmented epithelial cells and one or more rod photoreceptor cells of the human subject is transduced with the vector particle and wherein the REP1 is expressed in the one or more retinal pigmented epithelial cells and in the one or more rod photoreceptor cells, whereby the choroideremia is treated, arrested or palliated in the human subject.

2. The method according to claim 1, wherein the vector particle comprises SEQ ID NO: 1 or a derivative thereof wherein the derivative is missing one or more sequences selected from the group consisting of: one inverted terminal repeat (ITR) sequence, the replication (rep) gene sequence, and the capsid (cap) gene sequence.

3. The method according to claim 1, wherein the encoded REP1 comprises SEQ ID NO: 3.

4. The method according to claim 1, wherein the polynucleotide sequence encoding REP1 has at least 90% sequence identity with SEQ ID NO:2.

5. The method according to claim 1, wherein the promoter is a constitutively active promoter.

6. The method according to claim 1, wherein the promoter is a retinal-cell specific promoter.

7. The method according to claim 1 wherein the vector particle comprises one or more regulatory sequences.

8. The method according to claim 7 wherein the vector particle comprises a polynucleotide having at least 70% sequence identity with SEQ ID NO: 5.

9. The method of claim 1, wherein the promoter is an inducible promoter.

10. A method of treating a human subject suffering from choroideremia, the method comprising: administering to the subject by subretinal injection a therapeutically effective amount of an AAV2 vector particle comprising a polynucleotide encoding a Rab escort protein 1 (REP1) having at least 97% sequence identity with SEQ ID NO: 3, wherein said polynucleotide is operably linked to a chicken beta actin (CBA) promoter, wherein one or more retinal pigmented epithelial cells and one or more rod photoreceptor cells of the human subject is transduced with the vector particle and wherein the REP1 is expressed in the one or more retinal pigmented epithelial cells and in the one or more rod photoreceptor cells, whereby the choroideremia is treated, arrested or palliated in the human subject.

* * * * *